(12) United States Patent
Giorgetti

(10) Patent No.: US 12,239,622 B2
(45) Date of Patent: Mar. 4, 2025

(54) COMPOSITIONS COMPRISING AMINO ACIDS FOR USE IN THE PREVENTION AND TREATMENT OF LIVER DISEASES

(71) Applicant: Professional Dietetics International S.r.l., Milan (IT)

(72) Inventor: Paolo Luca Maria Giorgetti, Milan (IT)

(73) Assignee: PROFESSIONAL DIETETICS S.P.A., Milan (IT)

( * ) Notice: Subject to any disclaimer, the term of this patent is extended or adjusted under 35 U.S.C. 154(b) by 927 days.

(21) Appl. No.: 17/255,887

(22) PCT Filed: Apr. 2, 2019

(86) PCT No.: PCT/IB2019/052694
§ 371 (c)(1),
(2) Date: Dec. 23, 2020

(87) PCT Pub. No.: WO2020/003013
PCT Pub. Date: Jan. 2, 2020

(65) Prior Publication Data
US 2021/0260011 A1    Aug. 26, 2021

(30) Foreign Application Priority Data
Jun. 27, 2018   (IT) .................. 102018000006725

(51) Int. Cl.
| | | |
|---|---|---|
| *A61K 31/198* | (2006.01) | |
| *A61K 9/00* | (2006.01) | |
| *A61K 31/194* | (2006.01) | |
| *A61K 47/22* | (2006.01) | |
| *A61P 1/16* | (2006.01) | |

(52) U.S. Cl.
CPC .......... *A61K 31/198* (2013.01); *A61K 9/0053* (2013.01); *A61K 31/194* (2013.01); *A61K 47/22* (2013.01); *A61P 1/16* (2018.01)

(58) Field of Classification Search
CPC ................ A61K 31/194; A61K 31/198; A61K 2300/00; A61P 1/16
See application file for complete search history.

(56) References Cited

U.S. PATENT DOCUMENTS

| | | | |
|---|---|---|---|
| 6,537,969 B1 * | 3/2003 | Blass ...................... | A61P 25/28 514/23 |
| 7,982,066 B2 | 7/2011 | Scheele | |
| 9,597,367 B2 | 3/2017 | Wolfe et al. | |
| 10,226,441 B2 | 3/2019 | Higashi et al. | |
| 11,337,946 B2 | 5/2022 | Giorgetti | |
| 11,452,702 B2 | 9/2022 | Giorgetti | |
| 11,957,651 B2 | 4/2024 | Giorgetti | |
| 2003/0013761 A1 | 1/2003 | Joshi et al. | |
| 2003/0055099 A1 | 3/2003 | Martynyuk et al. | |
| 2013/0084378 A1 | 4/2013 | Jun et al. | |
| 2013/0237605 A1 | 9/2013 | Zemel et al. | |
| 2014/0315788 A1 | 10/2014 | Wolfe et al. | |
| 2016/0038565 A1 | 2/2016 | Khan | |
| 2018/0000764 A1 | 1/2018 | Hernández Miramontes | |
| 2020/0230093 A1 | 7/2020 | Giorgetti | |
| 2020/0253906 A1 | 8/2020 | Giorgetti | |
| 2021/0260011 A1 | 8/2021 | Giorgetti | |
| 2022/0110899 A1 | 4/2022 | Giorgetti | |
| 2022/0249418 A1 | 8/2022 | Giorgetti | |
| 2023/0067642 A1 | 3/2023 | Giorgetti | |
| 2023/0079527 A1 | 3/2023 | Giorgetti | |

FOREIGN PATENT DOCUMENTS

| | | | | |
|---|---|---|---|---|
| CA | 2972889 A1 | 9/2016 | | |
| EP | 2196203 B1 | 8/2012 | | |
| EP | 2676664 A1 | 12/2013 | | |
| EP | 2881112 B1 | 11/2019 | | |
| JP | 2007161642 A | 6/2007 | | |
| JP | 6023813 B2 * | 11/2016 | ............. | A23L 27/21 |
| WO | 2001051047 A1 | 7/2001 | | |
| WO | 2003013487 A2 | 2/2003 | | |
| WO | 2005034932 A2 | 4/2005 | | |
| WO | 2007/049818 A1 | 5/2007 | | |
| WO | 2012147901 A1 | 11/2012 | | |
| WO | 2016093104 A1 | 6/2016 | | |
| WO | 2016181335 A1 | 11/2016 | | |
| WO | WO-2016179657 A1 * | 11/2016 | ........... | A23L 33/175 |
| WO | 2017020121 A1 | 2/2017 | | |
| WO | 2017089612 A1 | 6/2017 | | |
| WO | 2018201024 A1 | 11/2018 | | |
| WO | 2019021135 A1 | 1/2019 | | |
| WO | 2019021137 A | 1/2019 | | |
| WO | 2019070750 A1 | 4/2019 | | |
| WO | 2020003013 A1 | 1/2020 | | |

(Continued)

OTHER PUBLICATIONS

Daher et al., J Clin Transl Hepatol. Mar. 28, 2018;6(1):69-78 (Year: 2018).*
Tapper et al., JAMA. 2023;329(18):1589-1602 (Year: 2023).*
Park Dong et al. (JP-6023813-B2, 2016, English Translation, pp. 1-16 (Year: 2016).*
MP Biomedical—Technical Information—AIN-93-Diet,pp. 1-3 (Year: 2023).*
Noguchi et al. WO/2007/049818 published Mar. 5, 2007, English Translation pp. 1-10 (Year: 2007).*
Tedesco et al.; "A specific amino acid formula prevents alcoholic liver disease in rodents"; Jan. 25, 2018; Am. J. Gastrointest. Liver Physiol.; 314: G566-G582; doi: 10.1152/ajpgi.00231.2017 (Year: 2018).*

(Continued)

*Primary Examiner* — Timothy P Thomas
(74) *Attorney, Agent, or Firm* — Nixon & Vanderhye P.C.

(57) ABSTRACT

Composition for use in the prevention and/or treatment of a liver disease in a mammal, the composition comprising an active agent, said active agent containing the amino acids leucine, isoleucine, valine, threonine, lysine and the carboxylic acids citric acid, succinic acid, malic acid.

20 Claims, No Drawings
Specification includes a Sequence Listing.

(56) References Cited

FOREIGN PATENT DOCUMENTS

WO  2022266480  12/2022

OTHER PUBLICATIONS

Nergiz et al.; "Organic acid content and composition of the olive fruits during ripening and its relationship with oil and sugar"; 2009; Scientia Horticulturae; 122: 216-220 (Year: 2009).*
International Search Report and Written Opinion of the ISA for PCT/IB2019/052694 mailed Jun. 25, 2019, 11 pages.
Database WPI Week 200744, May 3, 2007, Thomson Scientific, London, GB, XP002788927, 3 pages.
Tedeco et al., A specific amino acid formula prevents alcoholic liver disease in rodents, Am J Physiol Gastrointest Liver Physiol ., Epub Jan. 25, 2018, 314(5):G566-G582.
Brocca, I., et al., "Proteomic analysis of plasma after branched chain enriched mixture supplementation in mice", Journal of the International Society of Sports Nutrition, vol. 10, No. 1, Apr. 3, 2013, 5 pages.
International Search Report and Written Opinion of the ISA for PCT/182018/055425 mailed Nov. 2, 2018, 17 pages.
Bournat, J.C., et al., Mitochondrial Dysfunction in Obesity Current Opinion Endocrinol Obesity, Oct. 17, 2010, (5): 446-452.
Gorshinova et al., "Mitochondrial dysfunction as one of the mechanisms of impaired reproductive function in obesity." Akusherstvo i ginekologiya/Obstetrics and Gynecology, 2014; 7: 9-13.
Non-Final Office Action issued in co-pending U.S. Appl. No. 16/634,330, mailed Jun. 30, 2021.
International Search Report for PCT/IB2018/055428, mailed Nov. 6, 2018, 5 pages.
Written Opinion of the ISA for PCT/IB2018/055428, mailed Nov. 6, 2018, 7 pages.
Restriction Requirement issued in co-pending U.S. Appl. No. 16/634,330, mailed May 6, 2021.
Abdullah, Chowdhury S. et al., "Doxorubicin-induced cardiomyopathy associated with inhibition of autophagic degradation process and defects in mitochondrial respiration", Scientific Reports, vol. 9, No. 1, Feb. 14, 2019, 20 pp.
Chiechio, et al., "L-Acetylcarnitine: A Proposed Therapeutic Agent for Painful Peripheral Neuropathies", Current Neuropharmacology, vol. 4, No. 3, Jul. 1, 2006, pp. 233-237 (5 pages).
Choudhury, Aaheli Roy et al., "Mitochondrial determinants of cancer health disparities", Seminars in Cancer Biology, 47, 2017, pp. 125-146.
Damiani, Roberto Marques et al., "Pathways of cardiac toxicity: comparison between chemotherapeutic drugs doxorubicin and mitoxantrone", Archives of Toxicology, vol. 90, No. 9, Jun. 25, 2016, pp. 2063-2076.
Gilliam, Laura A.A. et al., "The anticancer agent doxorubicin disrupts mitochondrial energy metabolism and redox balance in skeletal muscle", Free Radical Biology and Medicine, vol. 65, Sep. 7, 2013, pp. 988-996.
Hall et al., "Lipid Peroxidation in Brain or Spinal Cord Mitochondria After Injury" J Bioenerg. Biomembr. Apr. 2016 ; 48(2): 169-174 (2017).
Hiensch, Anouk E. et al., "Doxorubicin-induced skeletal muscle atrophy: Elucidating the underlying molecular pathways", Acta Physiologica, vol. 229, No. 2, Oct. 10, 2019, 18 pp.
International Search Report and Written Opinion of the ISA for PCT/IB2018/055425 mailed Nov. 2, 2018, 17 pages.
International Search Report and Written Opinion of the ISA for PCT/IB2020/051027 dated Apr. 29, 2020, 11 pages.
International Search Report and Written Opinion of the ISA for PCT/IB2020/062301 dated Mar. 1, 2021 (12 pages).
International Search Report dated Mar. 16, 2021, for PCT/IB2020/062291, 5 pp and Written Opinion of the International Searching Authority dated Mar. 16, 2021, for PCT/IB2020/062291, 8 pp.
Keenan et al,, "Effects of carboxylic acids on the uptake of non-transferrin-bound iron by astrocytes, Neurochemistry International", 2010, 56: 843-849.
Nakagaichi, M., et al., "Effects of Exercise Training Plus Vespa Amino Acid Mixture (VAAM) Ingestion in Obese Women," Japanese Journal of Health Promotion, 3, 11-16, 2001 with English Abstract.
Nakamura, E., et al., "Assessment of Biological Age by Principal Component Analysis," Mechanisms of Ageing and Development, vol. 46. Issues 1-3, pp. 1-18, 1988, with English Translation of Office Action for JP Application No. 2019-566744 citing Nakamura attached to satisfy the requirement for a concise explanation of relevance.
Notice of Allowance mailed in U.S. Appl. No. 17/724,537 on Dec. 20, 2023.
Scholpa & Schnellmann, "Mitochondrial-Based Therapeutics for the Treatment of Spinal Cord Injury: Mitochondrial Biogenesis as a Potential Pharmacological Target." J Pharmacol Exp Ther 363:303-313, Dec. 2017.
Wang, X. et al., "Increases in mitochondrial biogenesis impair carcinogenesis at multiple levels" Molecular Oncology, Elsevier. Jul. 27, 2011., vol. 5, No. 5, pp. 399-409 (11 pages).
Wang et al., "Mitochondrial dysfunction in neurodegenerative diseases and the potential countermeasure," CNS Neurosci Ther. 25: 816-824 (2019).
Sullivan et al., "Mitochondrial Permeability Transition in CNS Trauma: Cause or Effect of Neuronal Cell Death?" Journal of Neuroscience Research, 2005, 79:231-239.

* cited by examiner

COMPOSITIONS COMPRISING AMINO ACIDS FOR USE IN THE PREVENTION AND TREATMENT OF LIVER DISEASES

This application is the U.S. national phase of International Application No. PCT/IB2019/052694 filed Apr. 2, 2019 which designated the U.S. and claims priority to IT patent application No. 102018000006725 filed Jun. 27, 2018, the entire contents of each of which are hereby incorporated by reference.

FIELD OF THE INVENTION

The present description relates generally to compositions comprising amino acids. More particularly, the description relates to compositions comprising amino acids for use in the prevention and/or treatment of liver diseases.

BACKGROUND

Liver diseases are among the most frequently occurring diseases caused by various unfavorable environment conditions, such as for example, parasites and viruses, drugs, toxic substances, alcoholism, and smoke. They are frequently chronic diseases with development of worsening clinical features. Chronic liver diseases are characterized by gradual destruction of the liver parenchyma over time, with inflammatory responses and fat accumulation, with fibrotic damage and activation of cellular transformations leading to cancer development in many cases. Thus, hepatic diseases may include steatosis, fibrosis, cirrhosis, and hepatocellular carcinoma as progressive clinical derangements of liver. Cirrhosis is the result of acute and chronic liver disease and is characterized by the replacement of liver tissue by fibrotic scar tissue and regenerative nodules leading to a progressive loss of liver function. Fibrosis and nodular regeneration results in the loss of the normal microscopic lobular architecture of the liver. Fibrosis represents the growth of scar tissue resulting from, for example, infection, inflammation, injury, and even healing. Over time, the fibrotic scar tissue slowly replaces the normal functional liver tissue resulting in a decreasing amount of blood flow to the liver leaving the liver incapable of fully processing nutrients, hormones, drugs, and poisons that are found in the blood stream. More common causes of cirrhosis include alcoholism, hepatitis C viral infections, ingestion of toxins, and many other possible causes also exist. As mentioned below, the epidemiologically most relevant disorder evolving to cirrhosis and possibly cancer is body fat gain and related hepatic fat accumulation. This fat accumulation can be due by two principal clinical conditions: alcohol abuse and obesity.

An excessive and chronic alcohol consumption may cause alcoholic liver disease (ALD), a major global health problem. The pathological features of ALD develop over long-term periods, including hepatic steatosis, steatohepatitis, cirrhosis until cancer.

Ethanol pathogenesis is contributed by multiple factors. Early events, such as mitochondrial damage, reactive oxygen species (ROS) generation, and fat accumulation seem to be direct outcomes of ethanol metabolism and are shared features between ALD and non-alcoholic liver disease or NAFLD (see below) (Mantena et al. 2008).

The cellular defense mechanisms against the detrimental effects of alcohol are not well understood. Autophagy, which is an important degradative cellular pathway which digests cellular proteins and organelles to obtain energy or eliminate damaged cellular structures, has been suggested to play a role in ALD, although understanding of these mechanisms is still fragmentary (Lin et al. 2015). Autophagy seems to play critical functions in both hepatocytes and nonparenchymal cells (i.e., macrophages and hepatic stem cells), influencing insulin sensitivity, lipid accumulation, hepatocellular injury, and the innate immune response.

Recent studies on mice and cell models have shown that acute ethanol ingestion activates autophagy in liver (Ding et al. 2010; Ni et al. 2013; Lin et al. 2013).

In contrast, chronic ethanol intoxication seems to suppress hepatic autophagy (Thomes et al. 2015; Cho et al. 2014). The inhibition of autophagy has been shown to worsen ethanol driven steatosis and liver injury in mice (Ding et al. 2010; Ni et al. 2013; Lin et al. 2013).

Conversely, pharmacological promotion of autophagy seems to alleviate ethanol-driven liver steatosis and liver injury (Lin et al. 2013). As a result, autophagy is regarded as a protective mechanism against the cytotoxic effects of ethanol and has emerged as target for the development of therapeutic agents for ALD.

As mentioned before, the second major cause of liver disorder is obesity, widely diffused in developed countries and increasing epidemiologically also in developing countries, and causing the so-called non-alcoholic fatty liver disease or NAFLD. Progression towards steatohepatitis, cirrhosis, and hepatocarcinoma represents an increasing emergence worldwide. Biochemical and molecular mechanisms involved in this condition are superimposable to those typically described in ALD.

Being an altered amino acid metabolism a hallmark of liver diseases, linked to both alcohol consumption and obesity development, specifically characterized by reduced levels of circulating branched-chain amino acids (BCAAs) (Charlton, 2006) there is a growing interest in the development of new therapeutic approaches based on amino acids supplementation as therapy for liver diseases.

SUMMARY OF THE INVENTION

The present description has the aim of providing new amino acid-based compositions effective in the prevention and treatment of liver diseases.

According to the present description, the above object is achieved thanks to the subject matter specifically recalled in the ensuing claims, which are understood as forming an integral part of this disclosure.

An embodiment of the present description provides a composition for use in the treatment of a liver disease in a mammal, the composition comprising an active agent, said active agent containing the amino acids leucine, isoleucine, valine, threonine, lysine and the carboxylic acids citric acid, succinic acid, malic acid.

In one or more embodiments, the active agent of the composition further contains one or more amino acids selected in the group consisting of histidine, phenylalanine, methionine, tryptophan, cysteine and tyrosine.

In a preferred embodiment, the liver disease may be selected in the group consisting of alcoholic liver disease (ADL), non-alcoholic liver disease (NAFDL) lipodystrophy, hepatitis, cirrhosis, hepatocellular carcinoma (HCC).

A further embodiment of the present disclosure provides a method of treating liver diseases in mammals, the method comprising selecting a composition comprising an active agent, said active agent containing the amino acids leucine, isoleucine, valine, threonine, lysine, and the carboxylic acids citric acid, succinic acid, and malic acid, administering the composition to treat a liver disease in mammals.

BRIEF DESCRIPTION OF THE DRAWINGS

The invention will now be described, by way of example only, with reference to the enclosed figures, wherein:

FIG. 1 shows gene expression shown as mRNA levels in HepG2 cells treated with different amino acid-based compositions and ethanol (EtOH) for 9 days (*P value<0.05 and **P<0.01 vs. CTRL cells).

FIG. 2 shows p62 protein level in HepG2 cells treated with different amino acid-based compositions and EtOH for 9 days (*P value<0.05 and **P<0.01 vs. CTRL cells; #P value<0.05 vs. EtOH-treated cells).

DETAILED DESCRIPTION OF PREFERRED EMBODIMENTS

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not interpret the scope or meaning of the embodiments.

Alcoholic liver disease (ALD) as well as non-alcoholic fatty liver disease (NAFLD) are major global health problem characterized by pathological features developing over long-term periods, including hepatic steatosis, steatohepatitis, cirrhosis, until cancer.

Early events in ethanol pathogenesis such as for example mitochondrial damage, reactive oxygen species (ROS) generation, and fat accumulation are shared features between ALD and NAFLD.

In addition, an altered amino acid metabolism has been shown to be a distinctive feature of liver disease, characterized by low levels of circulating branched-chain amino acids (BCAAs), and supplementation with BCAAs appeared to be associated with decreased frequency of complications of cirrhosis when prescribed as maintenance therapy (Charlton 2006).

The Inventor of the instant application found that by adding specific carboxylic acids to a composition comprising a combination of leucine, isoleucine, valine, threonine and lysine a high effectiveness in counteracting liver diseases, such as for example ALD and NAFLD, can be achieved.

The composition herein disclosed—comprising as active agent the amino acids leucine, isoleucine, valine, threonine, lysine in combination with three carboxylic acids, which are substrates of tricarboxylic acid cycle, including citric acid, succinic acid, and malic acid in specific amounts—has been shown to restore the altered amino acid metabolism induced by ethanol and consequently to prevent autophagy. Tricarboxylic acid cycle, (TCA cycle), also called Krebs cycle and citric acid cycle, which is carried out in the matrix of mitochondria, is the second stage of cellular respiration, the three-stage process by which living cells break down organic fuel molecules in the presence of oxygen to harvest the energy they need to grow and divide.

Compositions comprising the above stated active agent as well as compositions comprising the above stated active agent including further specific amino acids (listed in Table 1 below) are significantly more effective than a similar amino acid composition free of such specific carboxylic acids.

In one or more embodiments, in the composition herein disclosed the weight ratio between the total amount of citric acid, succinic acid and malic acid and the total amount of the amino acids leucine, isoleucine, valine, threonine, lysine is comprised between 0.05 and 0.3, preferably between 0.1 and 0.25.

In one or more embodiments, the active agent may further comprise one or more amino acids selected in the group consisting of histidine, phenylalanine, methionine, tryptophan, cysteine, and tyrosine.

In one or more embodiments, the carboxylic acids contained in the composition consist of citric acid, succinic acid, and malic acid.

In a further embodiment, the active agent of the composition herein disclosed may also include aspartic acid and/or ornithine L-alphaketoglutarate (OKG).

According to an embodiment, the composition comprises an active agent, the active agent consisting of leucine, isoleucine, valine, threonine, lysine, histidine, phenylalanine, methionine, tryptophan, cysteine, and optionally tyrosine, as well as citric acid, succinic acid, and malic acid, said amino acids being the sole amino acids contained in the composition. Citric acid, succinic acid, and malic acid may be the sole carboxylic acids contained in the composition.

In a further embodiment, the composition may comprise the amino acids isoleucine, leucine, and valine in an amount between 35% and 65% by weight, preferably between 42% and 56% by weight, with respect to the active agent weight.

In one or more embodiments, the weight ratio between leucine and citric acid is comprised between 5 and 1, preferably between 2.50 and 3.50.

In a further embodiment, the weight or molar amount of citric acid is higher than the weight or molar amount of each of malic acid and succinic acid. Preferably, the weight or molar amount of citric acid is higher than the weight or molar overall amount of malic acid plus succinic acid. In a further embodiment, the weight ratio between citric acid and the sum of malic acid and succinic acid is comprised between 1.0 and 4.0, preferably between 1.5 and 2.5. In a preferred embodiment, the citric acid:malic acid:succinic acid weight ratio is comprised between 10:1:1 and 2:1.5:1.5, preferably between 7:1:1 and 1.5:1:1, more preferably between 5:1:1 and 3:1:1. In a preferred embodiment the citric acid:malic acid:succinic acid weight ratio is 4:1:1.

According to some embodiments of the present disclosure, the preferred isoleucine:leucine molar ratio is comprised in the range 0.2-0.7, preferably in the range 0.30-0.60 and/or the preferred valine:leucine weight ratio is comprised in the range 0.2-0.70, preferably in the range 0.30-0.65.

In a further embodiment, the threonine:leucine molar ratio is comprised in the range of 0.10-0.90, preferably in the range 0.20-0.70 and/or the lysine:leucine weight ratio is comprised in the range of 0.20-1.00, preferably in the range 0.40-0.90.

In a preferred embodiment, the ratio between the overall molar amount of citric acid, malic acid, succinic acid and the overall molar amount of methionine, phenylalanine, histidine and tryptophan is higher than 1.35.

In one or more embodiments, the weight ratio between the sum of citric acid, malic acid, succinic acid and the sum of the branched chain amino acids leucine, isoleucine, valine is comprised between 0.1 and 0.4, preferably between 0.15 and 0.35.

In a further embodiment, the overall weight amount of the branched-chain amino acids leucine, isoleucine, valine plus threonine and lysine is higher than the overall weight amount of three carboxylic acids, such as citric acid, malic acid, and succinic acid. Preferably, the weight amount of the single carboxylic acid (citric acid, succinic acid, or malic acid) is less than the weight amount of each of the single amino acids leucine, isoleucine, valine, threonine, and lysine.

In a further embodiment, the overall molar amount of lysine and threonine is higher than the overall molar amount of the three carboxylic acids citric acid, succinic acid, malic acid. Preferably, the ratio between the overall molar amount of the three carboxylic acids citric acid, succinic acid, malic acid and the overall molar amount of lysine and threonine is comprised between 0.1 and 0.7, preferably between 0.15 and 0.55.

In one or more embodiments, the composition herein disclosed further comprises vitamins, preferably selected in the group of vitamins B, such as vitamin $B_1$ and/or vitamin $B_6$.

In a further embodiment of the present disclosure, the composition may include carbohydrates, additives and/or flavoring substances.

In a preferred embodiment, the composition is addressed to the prevention and/or treatment of a liver disease selected in the group consisting of fatty liver disease, lipodystrophy, hepatitis, cirrhosis, hepatocellular carcinoma (HCC).

In one or more embodiments, the liner disease is a fatty liver disease. The fatty liver disease may be caused by alcohol consumption (alcoholic fatty liver disease, ALD).

In one or more embodiments, the fatty liver disease is a non-alcoholic fatty liver disease (NFLD).

In one or more embodiments, the fatty liver disease may be due to drugs or toxins, such as for example amiodarone, methotrexate, diltiazem, highly active antiretroviral therapy, glucocorticoids, tamoxifen, mushroom poisoning.

Furthermore, in particular when preparing the compositions according to the instant disclosure, and specifically the active agent, the amino acid arginine is preferably avoided. In addition, further amino acids preferably avoided by the composition herein disclosed may be serine, proline, alanine. Such amino acids can be counterproductive or even harmful in some concentrations or stoichiometric ratios within the composition.

The amino acids disclosed in the instant application can be replaced by respective pharmaceutically acceptable derivatives, namely salts.

As will emerge clearly hereinafter, the administration of the compositions according to the present disclosure is particularly effective in the prevention and/or treatment of liver diseases.

In a preferred embodiment, the disclosed compositions may be used in the treatment of the alcoholic liver disease (ALD).

According to a further embodiment, the amino acid compositions may comprise pharmaceutically acceptable excipients, like for example proteins, vitamins, carbohydrates, natural and artificial sweeteners and/or flavouring substances. In a preferred embodiment, the pharmaceutically acceptable excipients may be selected from whey proteins, maltodextrins, fructose, calcium caseinate, fish oil, sucralose, sucrose esters, vitamin D3, group B vitamins.

For oral use, the compositions according to the description may be in the form of tablets, capsules, granules, gel, gelable powder, or powder.

Further specifications, in terms of amounts and ratios among the various amino acids provided for by the compositions are contained in the attached claims, which form an integral part of the technical teaching provided herein in relation to the invention.

EXAMPLES

Table 1 shows two different amino acid-based compositions tested in vitro on hepatocytes (HepG2 cells) and in vivo on ethanol-consuming rats, as disclosed below.

The composition named "BCAAem" in the following comprises an active agent containing the amino acids leucine, lysine, isoleucine, valine, threonine, cysteine, histidine, phenylalanine, methionine, tyrosine, tryptophan.

The composition named "alpha 5m (a5m)" comprises an active agent containing the same amino acids plus citric acid, succinic acid, and malic acid.

TABLE 1

| Compositions (% w/w) | BCAAem | α5m |
|---|---|---|
| L-Leucine | 30.01 | 31.0885 |
| L-Lysine HCl chlorhydrate | 19.58 | 16.903 |
| L-Isoleucine | 15 | 10.3628 |
| L-Valine | 15 | 10.3628 |
| L-Threonine | 8.4 | 7.254 |
| L-Cysteine | 3.6 | 3.1089 |
| L-Histidine | 3.6 | 3.1089 |
| L-Phenylalanine | 2.4 | 2.0726 |
| L-Methionine | 1.2 | 1.0363 |
| L-Tyrosine | 0.72 | 0.6218 |
| L-Tryptophan | 0.48 | 2.0726 |
| OKG(ornithine L-α ketoglutarate) | — | — |
| Vitamin B1 (thiamine chlorhydrate) | — | 0.004 |
| Vitamin B6 (piridoxine chlorhydrate) | — | 0.0038 |
| Citric acid anhydrous | — | 8.0000 |
| Malic acid | — | 2.0000 |
| Acid L-aspartic | — | — |
| Succinic acid | — | 2.0000 |
| Ratio Leucine:Isoleucine:Valine | 2:1:1 | 3:1:1 |

The compositions of Table 1 above may be prepared first by sifting all the components with a 0.8 mesh. To obtain a pre-mixture, each ingredient (in an amount <10% by weight of the total amount) is put in a polyethylene bag together with a portion of L-lysine HCl so as to obtain 10% of the weight of the total composition. The bag is then manually shaken for 5 minutes. The pre-mixture is then loaded in a mixer (Planetaria) together with the remainder of the ingredients and mixed for a period of 15 minutes at 120 rpm to obtain a homogeneous final composition.

Methods

Animals and Treatments

The experimental protocol was approved and conducted in accordance with the European Communities Council Directive of Nov. 24, 1986 (86/609/EEC), and the Italian Ministry of Heath, and complied with The National Animal Protection Guidelines.

Male Wistar rats (3 months old) from Charles River (Calco, Como, Italy) were used for the experimental analysis disclosed hereinafter.

Animals were housed separately in clean polypropylene cages and divided into six groups:

1) the pair-fed group (pair-fed CTRL, n=6) was fed with a control liquid diet, in which ethanol (EtOH) was replaced by isocaloric maltose dextran;
2) the EtOH group (EtOH, n=7) was fed with a Lieber-DeCarli liquid diet containing EtOH ad libitum [gradually increasing amount of EtOH, reaching 36% of caloric intake after 1 week, corresponding to a final concentration of 6.2% (vol/vol)];
3) the BCAAem group (BCAAem, n=6) fed with a control liquid diet, in which EtOH was replaced by isocaloric maltose dextran, and supplemented with the branched-chain amino acid composition ("BCAAem" in Table 1) that provided 1.5 g/kg/day BCAAem;
4) the alpha 5 group (α5m, n=6) fed with a control liquid diet, in which EtOH was replaced by isocaloric maltose dextran, and supplemented with the amino acid composition ("α5m" in Table 1) that provided 1.5 g/kg/day;
5) the EtOH plus BCAAem group (EtOH+BCAAem, n=7) fed with a Lieber-DeCarli liquid diet containing EtOH and BCAAem composition ad libitum; and
6) the EtOH plus α5m group (EtOH+α5m, n=7), fed with a Lieber-DeCarli liquid diet containing EtOH and α5m composition ad libitum.

Sample Preparation

Liver (n=4 animals/group) was weighted, homogenized in cold methanol:water (v/v, 1:1), and extracted according to Want et al. (Want et al. 2013). The vacuum dried samples were suspended in 120 µl/50 mg tissue of methanol:1 mM TDFHA=1:1 and centrifuged at 16,000 g for 10 minutes at 4° C. Two µl of surnatant were directly loaded onto the UPLC-mass spectrometer and analyzed as reported below. Four technical replicates for each sample were run using the three different methods.

Chromatography and Amino Acid Quantification in Liver

Standard amino acids were purchased from Sigma (Milan, Italy). Each amino acid stock solutions were prepared at 1 mg/ml in water, diluted to the final concentration of 3 pmol/µl, and directly infused by syringe at 10 µl/min into the TripleTOF 5600+ mass spectrometer (AB Sciex, Milan, Italy). Thus, declustering potential (DP) and collision energy (CE) were optimized for each amino acid.

Next, three mixtures of amino acids were prepared on the basis of DP and CE values: MIX 1, containing threonine, asparagine, tyrosine, and serine, and analyzed with DP: 30 V, CE: 15 V; MIX 2, containing glycine, alanine, leucine, isoleucine, valine, proline, histidine, methionine, aspartic acid, glutamine, and phenylalanine, and analyzed with DP: 40 V, CE: 15 V; and MIX 3, containing glutamic acid, lysine, arginine, and tryptophan, and analyzed with DP: 80 V, CE: 18 V.

The source parameters were: gas 1: 33 psi, gas 2: 58 psi, curtain gas: 25 psi, temperature: 500° C., and ISVF (Ion-Spray Voltage Floating): 5500 V.

In order to obtain calibration curves, technical quadruplicates of different amounts (10, 33, 50, 100, 200, 400 pmol) of the three mixtures were injected into the mass spectrometer upon UPLC separation, using the UPLC 1290 (Agilent Technologies Italia, Cernusco sul Naviglio, Milan, Italy). The chromatographic column was from Waters, Acquity HSS T3 C18 2.1×100 mm, 1.7 µm, while the mobile phase was A: 1 mM TDFHA (tridecafluoroheptanoic acid) in water; B: 1 mM TDFHA in acetonitrile. A gradient of B from 12.5% to 26.5% in 4 min, followed by a ramp from 26.5 to 92% in 3.5 min was used to separate all of the amino acids, with a flow rate of 0.35 ml/min and a column temperature of 65° C. as described (Le et al., 2014).

The autosampler was set at 4° C. Calibration curves were plotted using chromatographic peak areas and a weighted regression (1/x for all compounds except asparagine, tyrosine, valine, and glutamic acid, which were fit to 1/x2) by means of MultiQuant software version 2.1 (SCIEX). Quantitative values for each amino acid (pmol) in the rat liver samples were obtained by relating chromatographic peak areas to those derived from externally run calibration standards and normalized to tissue (mg).

Cell Culture and Treatment

Human HCC HepG2 cells were purchased from the American Type Culture Collection (HB-8065; ATCC, Manassas, Va.). Cells were routinely cultured in RPMI-1640 medium, supplemented with 10% fetal bovine serum, penicillin (100 U/mL), and streptomycin (100 µg/mL), in an atmosphere with 5% CO2 at 37° C. Two million HepG2 cells were seeded per 75 cm$^2$ flask (Corning Inc., Corning, N.Y.).

Six h after seeding, 75 mM (0.34%) EtOH and 1% BCAAem or α5m were added, alone or in combination. Untreated cells were plated as controls. Every 24 h, media were replaced in both control and treatment flasks, with fresh media, with or without EtOH and BCAAem or α5m, respectively. Four days after seeding, cells were trypsinized and seeded into new flasks, at 2 million viable cells per flask, with daily media changes, as described before (Pochareddy et al. 2012). Five days after the split process (a total of 9 days with or without EtOH, BCAAem or α5m, or EtOH plus BCAAem or α5m), the cells were harvested as reported below for the different assays.

Quantitative RT-PCR Analysis

Quantitative RT-PCR reactions were performed as described (Tedesco et al. 2008) and run with the iQ Sybr-Greenl SuperMix (Bio-Rad; Segrate, Italy) on an iCycler iQ Real-Time PCR detection system (Bio-Rad).

Briefly, RNA was isolated from tissue using the RNeasy® Tissue Mini Kit (Qiagen, Milan, Italy). cDNA was synthesized using iScript™ cDNA Synthesis Kit (Bio-Rad Laboratories, Segrate, Italy).

Primers were designed using Beacon Designer 2.6 software from Premier Biosoft International (sequences are reported in Table 2 below). The cycle number at which the various transcripts were detectable (threshold cycle, CT) was compared to that of TBP, referred to as ΔCT. The gene relative levels were expressed as 2-(ΔΔCT), in which ΔΔCT equals ΔCT of EtOH- or BCAAem- or CAA mixture-treated rat (or treated HepG2 cells) minus ΔCT of the control rat (or untreated HepG2 cells).

TABLE 2

| Gene | Primer | Sequence | SEQ ID. | $T_a$ |
|---|---|---|---|---|
| PGC-1α | Sense 5'-3' | 5'-GACCCCAGAGTCACCAAATGAC-3' | No.1 | 60 |
| | Antisense 5'-3' | 5'-TTGGTTGGCTTTATGAGGAGGA-3' | No.2 | |

TABLE 2-continued

| Gene | Primer | Sequence | SEQ ID. | $T_a$ |
|------|--------|----------|---------|-------|
| Tfam | Sense 5'-3' | 5'-AGATTGGGGTCGGGTCAC-3' | No.3 | 60 |
|      | Antisense 5'-3' | 5'- GACAACTTGCCAAGACAGATG-3' | No.4 | |
| NRF1 | Sense 5'-3' | 5'-ACTCGTGTGGGACAGCAAGC-3' | No.5 | 60 |
|      | Antisense 5'-3' | 5'-ATGGTGAGAGGCGGCAGTTC-3' | No.6 | |
| Cytc | Sense 5'-3' | 5'-CGTTGTGCCAGCGACTAAAAA-3' | No.7 | 60 |
|      | Antisense 5'-3' | 5'-TTCCGCCCAAAGAGACCA-3' | No.8 | |
| TBP  | Sense 5'-3' | 5'-AGGCACCACAGCTCTTCCAC-3' | No.9 | 60 |
|      | Antisense 5'-3' | 5'-CCCAGAACTCTCCGAAGCTG-3' | No.10 | |

$T_a$ temperature of annealing (° C.); Accession number PGC-1α: NM_013261; Accession number Tfam: NM_009360.4; Accession number NRF1: NM_005011; Accession number Cytc: JF919224.1; Accession number TBP: NG_051572 was used to normalize gene expression.

Western Blot Analysis

Protein extracts were obtained from liver with T-PER Mammalian Protein Extraction Reagent (Pierce, Thermo-Scientific, Rockford, USA) as described by the manufacturer, in the presence of protease and phosphatase inhibitor cocktail (Sigma Aldrich, Milan, Italy). Protein content was measured by the bicinchoninic acid protein assay (BCA, Pierce, Euroclone, Milan, Italy), and 50 µg of proteins were run on SDS-PAGE under reducing conditions. The separated proteins were then electrophoretically transferred to a nitrocellulose membrane (Bio-Rad Laboratories, Segrate, Italy). Proteins of interest were revealed with specific antibodies: anti-p62 and anti-α-actin (all from Cell Signaling, Euroclone, Milan, Italy), at 1:1000 dilution each one. The immunostaining was detected using horseradish peroxidase-conjugated anti-rabbit or anti-mouse immunoglobulin for 1 h at room temperature. The amount of protein was measured using SuperSignal Substrate (Pierce, Euroclone, Milan, Italy), and quantified by densitometry with IMAGEJ software image analyser.

Statistical Analysis

For all gene expression data, two-sided paired-sample t tests were used to compare values between control and treated cells. A P value<0.05 was considered statistically significant.

Results

Composition α5m is More Effective than BCAAem Composition to Restore Hepatic Mitochondrial Biogenesis and Function Impaired by EtOH Consumption The capacity of BCAAem and α5m compositions to ameliorate impaired mitochondrial biogenesis and function due to EtOH exposure was evaluated. In order to investigate the molecular mechanisms involved in the effects exerted by BCAAem and α5m compositions an in vitro model of hepatic EtOH toxicity was used.

To this end, hepatic HepG2 cells were exposed to 75 mM EtOH, with or without BCAAem α5m compositions, for 9 days. Proliferator-activated receptor y coactivator 1α (PGC-1α), nuclear respiratory factor-1 (NRF-1), mitochondrial DNA transcription factor A (Tfam), and cyt c mRNA levels were unchanged or slightly lower in HepG2 cells exposed to 75 mM EtOH for 9 days, than in untreated control cells (FIG. 1).

However, BCAAem and α5m composition administration for 9 days increased PGC-1α and Tfam mRNA levels with respect to both untreated and EtOH treated cells (FIG. 1).

Notably, the efficacy of α5m composition to improve hepatic mitochondrial biogenesis markers was statistically higher than that of BCAAem.

Analysis of Autophagy

Autophagic flux can be inferred by combining several markers, including protein levels of p62/SQSTM1 in addition to the LC3II/LC3I ratio, Beclin1, and Atg7, and 4EBP1 phosphorylation (Klionsky et al., 2016). p62/SQSTM1 has been shown to be incorporated in autophagosomes and degraded in autolysosomes. Hence, a reduced p62/SQSTM1 protein level is indicative of increased autophagy (Klionsky et al. 2016).

As shown in FIG. 2 of the instant application, p62 protein level was lower in HepG2 cells exposed to 75 mM EtOH for 9 days than in untreated control cells.

However, after 9 days administration of the BCAAem or α5m compositions p62 protein level was higher with respect to the p62 level of both untreated and EtOH treated cells.

Also in this case, the efficacy of the α5m composition was statistically higher than that of the BCAAem composition.

Liver Amino Acid Quantification

As disclosed above, an altered amino acid metabolism—specifically low levels of circulating BCAAs—has been shown to be a distinctive feature of alcoholic liver disease (Charlton, 2006).

Data provided in the following refers to the effects of the BCAAem or α5m compositions on the amino acid metabolism in liver of chronically EtOH-consuming rats.

To this aim, free amino acid levels were measured using chromatography analysis in liver tissue of rats consuming EtOH alone or in combination with tested compositions.

As reported in Table 3, the supplementation of the BCAAem and α5m compositions was ineffective on the level of Arginine, Leucine and Tryptophan. In contrast, the EtOH consumption led to a reduction of the levels of these amino acids in liver.

Interestingly, the administration of the BCAAem and α5m compositions in the EtOH-consuming rats prevented Arginine, Leucine, and Tryptophan reductions.

Also, Isoleucine, Serine, Tyrosine, and Valine concentrations were lower in liver of mice exposed to EtOH-containing diet.

Although BCAAem supplementation was unable to prevent their decline, α5m supplementation on the contrary was also effective in preventing the EtOH-induced reduction of isoleucine and valine.

Concentrations of the remaining amino acids were not statistically different among groups.

These results are consistent with the specific ability of α5m composition compared to BCAAem composition in renormalizing levels of BCAAs in liver samples of EtOH-consuming rats.

TABLE 3

| | CTRL | BCAAem | α5m | EtOH | EtOH + BCAAem | EtOH + α5m |
|---|---|---|---|---|---|---|
| Alanine | 670.1 ± 65.7 | 832.0 ± 25.0 | 932.0 ± 34.0 | 691.2 ± 128.0 | 679.0 ± 110.0 | 703.0 ± 90.0 |
| Arginine | 6.6 ± 0.7 | 4.3 ± 0.8 | 5.3 ± 0.7 | 2.46 ± 0.5* | 4.3 ± 0.7# | 4.6 ± 0.5# |
| Asparagine | 8.9 ± 2.4 | 7.9 ± 2.7 | 9.1 ± 1.7 | 8.1 ± 2.1 | 6.9 ± 2.8 | 7.8 ± 2.3 |
| Glycine | 409.8 ± 78.2 | 479.8 ± 32.0 | 442.8 ± 54.0 | 424.1 ± 52.0 | 440.7 ± 67.2 | 416.7 ± 59.2 |
| Glutamic acid | 5232.0 ± 430.0 | 5394.0 ± 438.0 | 5193.0 ± 328.0 | 5970.5 ± 832.0 | 4717.70 ± 85 | 4928.67 ± 550 |
| Histidine | $527.9 \cdot 10^3 \pm 80.3 \cdot 10^3$ | $606.8 \cdot 10^3 \pm 10.8 \cdot 10^3$ | $705.8 \cdot 10^3 \pm 10.5 \cdot 10^3$ | $461.1 \cdot 10^3 \pm 44.6 \cdot 10^3$ | $406.0 \times 10^3 \pm 19.3 \cdot 10^3$ | $606.0 \times 10^3 \pm 11.3 \cdot 10^3$ |
| Isoleucine | 141.9 ± 29.7 | 144.4 ± 4.5 | 153.4 ± 3.4 | 92.9 ± 16.6* | 93.2 ± 17.9* | 143.1 ± 16.4# |
| Leucine | 195.0 ± 56.4 | 189.1 ± 81.9 | 197.1 ± 71.6 | 110.2 ± 18.8* | 188.9 ± 92.4# | 195.8 ± 82.3# |
| Lysine | 72.2 ± 16.8 | 90.5 ± 19.7 | 87.5 ± 17.8 | 62.3 ± 9.6 | 53.3 ± 6.4 | 67.2 ± 7.3 |
| Methion. | 12.9 ± 5.5 | 17.9 ± 5.3 | 16.5 ± 3.9 | 11.9 ± 3.9 | 17.8 ± 4.7 | 15.9 ± 5.1 |
| Phenylal. | 32.0 ± 13.2 | 36.4 ± 4.8 | 39.2 ± 3.3 | 27.7 ± 10.2 | 28.8 ± 5.2 | 35.6 ± 4.5 |
| Proline | 33.7 ± 5.2 | 33.5 ± 1.3 | 33.9 ± 2.3 | 27.2 ± 8.7 | 24.6 ± 4.2 | 31.7 ± 3.9 |
| Serine | 348.7 ± 33.9 | 362.4 ± 9.9 | 385.4 ± 10.9 | 220.7 ± 58.4* | 215.4 ± 43.0* | 342.4 ± 39.1* |
| Threonine | 55.5 ± 2.41 | 52.2 ± 2.0 | 51.2 ± 1.7 | 52.9 ± 2.5 | 51.5 ± 2.2± | 53.5 ± 1.7 |
| Tryptop. | $1252.8 \cdot 10^3 \pm 226.4 \cdot 10^3$ | $1350.4 \cdot 10^3 \pm 74.54 \cdot 10^3$ | $1299.4 \cdot 10^3 \pm 99.4 \cdot 10^3$* | $787.1 \cdot 10^3 \pm 112.7 \cdot 10^{3*}$ | $1038.2 \cdot 10^3 \pm 169.9 \cdot 10^3$# | $1178.2 \cdot 10^3 \pm 178.9 \cdot 10^3$# |
| Tyrosine | 514.5 ± 63.3 | 382.6 ± 19.7 | 472.6 ± 29.7 | 311.7 ± 71.89* | 274.6 ± 39.7* | 354.8 ± 35.6* |
| Valine | 429.9 ± 46.7 | 455.3 ± 17.7 | 564.3 ± 20.7 | 291.9 ± 61.1 | 290.8 ± 48.9± | 450.8 ± 62.7# |

Values are reported as means ± SD (pmol/mg of tissue), n = 4 animals/group;
*$P < 0.05$ vs. CTRL group;
P value $< 0.05$ vs. EtOH group.

In summary, in vitro and in vivo results show that dietary supplementation with a composition comprising an active agent, the active agent containing a combination of leucine, isoleucine, valine, threonine, lysine, citric acid, succinic acid, and malic acid is significantly effective in preventing mitochondrial damage of hepatocytes exposed to EtOH.

This effect is also accompanied by reduction of autophagy (i.e., increase of p62 protein levels) which is increased (i.e., decrease of p62 protein levels) by EtOH exposure.

EtOH per se may enhance autophagy to compensate the EtOH toxicity and, in particular, the mitochondrial damage that is evident in hepatocytes exposed to alcohol and in liver of animals consuming alcohol.

In fact, autophagy is a cellular mechanism aimed to eliminate malfunction organelles, including mitochondria. When hepatocytes are exposed to alcohol and mitochondrial function is reduced, an increased autophagy, as also disclosed in the instant application, is useful to eliminate malfunctioning mitochondria.

The amino-acid compositions herein disclosed, comprising a combination of leucine, isoleucine, valine, threonine, lysine, with citric acid, succinic acid, and malic acid, is able to prevent the mitochondrial damage, so that cell does not need autophagy to maintain its energetic function. Consequently, autophagy decreases (as shown by the increased p62 protein level, shown in the instant application).

Moreover, and most importantly, the disclosed compositions have been found to be very effective in restoring the free BCAA, Arginine, and Tryptophan concentrations in liver of the EtOH-consuming rats.

Notably, preliminary results suggest that the amino acid compositions herein disclosed comprising a combination of leucine, isoleucine, valine, threonine, lysine, with citric acid, succinic acid, and malic acid is also able to reduce diameter of lipid droplets in hepatocytes of mice exposed for 6 months to a high-fat diet (HFD, 60% calories from fat), a widely used mouse model of NAFLD. Altogether these results strongly support the notion that the amino acid compositions herein disclosed and active in alcohol-dependent liver toxicity, may be healthy in prevention of NAFLD development and worsening.

From the foregoing, it emerges clearly how the compositions according to the instant disclosure are useful for the prevention and/or treatment of liver diseases worldwide affecting large adult population, with increasing societal costs.

REFERENCES

Charlton M. (2006) Branched-Chain Amino Acid Enriched Supplements as Therapy for Liver Disease. J Nutr 136: 295S-298S.

Cho H I, Choi J W, Lee S M (2014) Impairment of autophagosome-lysosome fusion contributes to chronic ethanol-induced liver injury. Alcohol 48:717-725.

Cooper G M and Hausman R E (2009) La cellula. Un approccio molecolare. Bioenergetica e metabolismo. Mitocondri, cloroplasti e perossisomi. Piccin 11: 432-468.

Ding W X, Li M, Chen X, Ni H M, Lin C W, Gao W, Lu B, Stolz D B, Clemens D L, Yin X M (2010) Autophagy reduces acute ethanol-induced hepatotoxicity and steatosis in mice. Gastroenterology 139:1740-1752.

Jung C H, Ro S-H, Cao J, Otto N M, Kim D-H (2010) mTOR regulation of autophagy. FEBS Lett 584:1287-1295.

Klionsky D J et al (2016) Guidelines for the use and interpretation of assays for monitoring autophagy (3rd edition). Autophagy 12:1-222.

Lin C W, Zhang H, Li M, Xiong X, Chen X, Chen X, Dong X C, Yin X M (2013) Pharmacological promotion of autophagy alleviates steatosis and injury in alcoholic and non-alcoholic fatty liver conditions in mice. J Hepatol 58:993-999.

Lin Wang, Bilon Khambu, Hao Zhang, Xiao-Ming Yin (2015) Autophagy in alcoholic liver disease, self-eating triggered by drinking. Clinics and research in hepatology and gastroenterology 39, S2-S6.

Le A, Ng A, Kwan T, Cusmano-Ozog K, Cowan T M. (2014) A rapid, sensitive method for quantitative analysis of underivatized amino acids by liquid chromatography-tandem mass spectrometry (LC-MS/MS). J Chromatogr B Analyt Technol Biomed Life Sci 944: 166-174.

Mantena S K, King A L, Andringa K K, Eccleston H B and Bailey S M (2008) Mitochondrial dysfunction and oxidative stress in the pathogenesis of alcohol- and obesity-induced fatty liver diseases. Free Radical Biology and Medicine 44: 1259-1272.

Ni H-M, Du K, You M, Ding W-X (2013) Critical role of FoxO3a in alcohol-induced autophagy and hepatotoxicity. Am J Pathol 183:1815-1825.

Pochareddy S, Edenberg H J. (2012) Chronic alcohol exposure alters gene expression in HepG2 cells. Alcohol Clin Exp Res 36: 1021-1033.

Tedesco L, Valerio A, Cervino C, Cardile A, Pagano C, Vettor R, Pasquali R, Carruba M O, Marsicano G, Lutz B, Pagotto U, and Nisoli E. (2008) Cannabinoid type 1 receptor blockade promotes mitochondrial biogenesis through endothelial nitric oxide synthase expression in white adipocytes. Diabetes 57: 2028-2036.

Thomes P G, Trambly C S, Fox H S, Tuma D J, Donohue T M Jr (2015) Acute and chronic ethanol administration differentially modulate hepatic autophagy and transcription factor E B. Alcohol Clin Exp Res 39:2354-2363. https://doi.org/10.1111/acer.12904.

Valerio A, D'Antona G, Nisoli E. (2011) Branched-chain amino acids, mitochondrial biogenesis, and healthspan: an evolutionary perspective. Aging 3: 464-478.

Want E J, Masson P, Michopoulos F, Wilson I D, Theodoridis G, Plumb R S, Shockcor J, Loftus N, Holmes E, Nicholson J K. (2013) Global metabolic profiling of animal and human tissues via UPLC-MS. Nat Protoc 8: 17-32.

---

The invention claimed is:

1. A method of treating liver cirrhosis, alcoholic liver disease (ALD) or non-alcoholic fatty liver disease (NAFLD), comprising administering to a subject in need thereof a therapeutic amount of a composition, wherein the composition comprises an active agent, said active agent containing the amino acids leucine, isoleucine, valine, threonine, lysine and the carboxylic acids citric acid, succinic acid, malic acid.

2. The method according to claim 1, wherein the active agent comprises an overall amount of citric acid, malic acid and succinic acid and an overall amount of leucine, isoleucine, valine, lysine and threonine, wherein the weight ratio between the overall amount of citric acid, malic acid and succinic acid and the overall amount of leucine, isoleucine, valine, lysine and threonine is between 0.05 and 0.3.

3. The method according to claim 1, wherein the active agent comprises an overall amount of citric acid, malic acid and succinic acid and an overall amount of leucine, isoleucine and valine, wherein the weight ratio between the overall amount of citric acid, malic acid and succinic acid and the overall amount of leucine, isoleucine and valine is between 0.1 and 0.4.

4. The method according to claim 1, wherein the active agent comprises a weight ratio between citric acid and the sum of malic acid and succinic acid is between 1.0 and 4.0.

5. The method according to claim 1, wherein the active agent comprises a weight ratio of citric acid:malic acid:succinic acid between 10:1:1 and 2:1.5:1.5.

6. The method according to claim 1, wherein said active agent further comprises at least one amino acid selected from the group consisting of histidine, phenylalanine, methionine, tryptophan, tyrosine and cysteine.

7. The method according to claim 1, wherein said active agent further comprises histidine, phenylalanine, methionine, tryptophan and cysteine.

8. The method according to claim 1, wherein the active agent comprises an overall molar amount of citric acid, malic acid and succinic acid and an overall molar amount of methionine, phenylalanine, histidine and tryptophan, wherein the ratio between the overall molar amount of citric acid, malic acid and succinic acid and the overall molar amount of methionine, phenylalanine, histidine and tryptophan is higher than 1.35.

9. The method according to claim 1, wherein the active agent comprises an overall molar amount of the three carboxylic acids citric acid, succinic acid and malic acid and an overall molar amount of lysine and threonine, wherein the ratio between the overall molar amount of the three carboxylic acids citric acid, succinic acid and malic acid and the overall molar amount of lysine and threonine is between 0.10 and 0.70.

10. The method according to claim 1, wherein the active agent comprises a weight or molar amount of citric acid, an overall weight or molar amount of malic acid and succinic acid, wherein the weight or molar amount of citric acid is higher than the overall weight or molar amount of malic acid and succinic acid.

11. The method according to claim 1, wherein the active agent comprises a weight ratio between leucine and citric acid between 5 and 1.

12. The method according to claim 1, wherein the composition further comprises one or more vitamins.

13. The method according to claim 2, wherein the weight ratio between the overall amount of citric acid, malic acid and succinic acid and the overall amount of leucine, isoleucine, valine, lysine and threonine is between 0.1 and 0.25.

14. The method according to claim 3, wherein the weight ratio between the overall amount of citric acid, malic acid and succinic acid and the overall amount of leucine, isoleucine and valine is between 0.15 and 0.35.

15. The method according to claim 4, wherein the active agent comprises a weight ratio between citric acid and the sum of malic acid and succinic acid between 1.5 and 2.5.

16. The method according to claim 5, wherein the active agent comprises a weight ratio of citric acid:malic acid:succinic acid between 7:1:1 and 1.5:1:1.

17. The method according to claim 5, wherein the active agent comprises a weight ratio of citric acid:malic acid:succinic acid between 5:1:1 and 3:1:1.

18. The method according to claim 7, wherein said active agent further comprises tyrosine.

19. The method according to claim 9, wherein the ratio between the overall molar amount of the three carboxylic acids citric acid, succinic acid and malic acid and the overall molar amount of lysine and threonine is between 0.15 and 0.55.

20. The method according to claim 11, wherein the active agent comprises a weight ratio between leucine and citric acid between 2.50 and 3.50.

* * * * *

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: PGC1N1 Sense 5' - 3'

<400> SEQUENCE: 1
gaccccagag tcaccaaatg ac                                              22

<210> SEQ ID NO 2
<211> LENGTH: 22
<212> TYPE: DNA
<213> ORGANISM: Artificial Sequence
<220> FEATURE:
<223> OTHER INFORMATION: PGC1N1 antisense 5' - 3'

<400> SEQUENCE: 2
ttggttggct ttatgaggag ga                                              22

<210> SEQ ID NO 3
<211> LENGTH: 18
<212> TYPE: DNA
<213> ORGANISM: Artificial Sequence
<220> FEATURE:
<223> OTHER INFORMATION: Tfam sense 5' - 3'

<400> SEQUENCE: 3
agattggggt cgggtcac                                                   18

<210> SEQ ID NO 4
<211> LENGTH: 21
<212> TYPE: DNA
<213> ORGANISM: Artificial Sequence
<220> FEATURE:
<223> OTHER INFORMATION: Tfam antisense 5' - 3'

<400> SEQUENCE: 4
gacaacttgc caagacagat g                                               21

<210> SEQ ID NO 5
<211> LENGTH: 20
<212> TYPE: DNA
<213> ORGANISM: Artificial Sequence
<220> FEATURE:
<223> OTHER INFORMATION: NRF1 sense 5' - 3'

<400> SEQUENCE: 5
```

```
actcgtgtgg gacagcaagc                                                    20

<210> SEQ ID NO 6
<211> LENGTH: 20
<212> TYPE: DNA
<213> ORGANISM: Artificial Sequence
<220> FEATURE:
<223> OTHER INFORMATION: NRF1 antisense 5' - 3'

<400> SEQUENCE: 6
atggtgagag gcggcagttc                                                    20

<210> SEQ ID NO 7
<211> LENGTH: 21
<212> TYPE: DNA
<213> ORGANISM: Artificial Sequence
<220> FEATURE:
<223> OTHER INFORMATION: Cytc Sense 5'-3'

<400> SEQUENCE: 7
cgttgtgcca gcgactaaaa a                                                  21

<210> SEQ ID NO 8
<211> LENGTH: 18
<212> TYPE: DNA
<213> ORGANISM: Artificial Sequence
<220> FEATURE:
<223> OTHER INFORMATION: Cytc antisense 3'-5'

<400> SEQUENCE: 8
ttccgcccaa agagacca                                                      18

<210> SEQ ID NO 9
<211> LENGTH: 20
<212> TYPE: DNA
<213> ORGANISM: Artificial Sequence
<220> FEATURE:
<223> OTHER INFORMATION: TBP sense 5'-3'

<400> SEQUENCE: 9
aggcaccaca gctcttccac                                                    20

<210> SEQ ID NO 10
<211> LENGTH: 20
<212> TYPE: DNA
<213> ORGANISM: Artificial Sequence
<220> FEATURE:
<223> OTHER INFORMATION: TBP antisense 5'-3'

<400> SEQUENCE: 10
cccagaactc tccgaagctg                                                    20
```